US00PP10032P

United States Patent [19]

Cosner et al.

[11] Patent Number: Plant 10,032

[45] Date of Patent: Sep. 16, 1997

[54] IMPATIENS PLANT NAMED 'TIOGA PEACH'

[76] Inventors: Harlan B. Cosner; Sue L. Cosner, both of P.O. Box 173, Broadbent, Oreg. 97414

[21] Appl. No.: 529,572

[22] Filed: Sep. 18, 1995

[51] Int. Cl.[6] ..... A01H 5/00

[52] U.S. Cl. ..... Plt./87.6

[58] Field of Search ..... Plt./87.6

*Primary Examiner*—James R. Feyrer

*Attorney, Agent, or Firm*—C. A. Whealy

[57] ABSTRACT

A distinctive cultivar of Impatiens plant named Tioga Peach, characterized by its large salmon-pink flowers; flowers held above the foliage; consistently double and symmetrical flower form; numerous flowers per plant; freely branching plant habit; and mounded plant form.

1 Drawing Sheet

1

The present invention relates to a new and distinct cultivar f Impatiens plant, botanically known as *Impatiens walleri-na*, and hereinafter referred to by the cultivar name Tioga each.

The new cultivar is a product of a planned breeding rogram conducted by the inventors in Coquille, Oreg. The bjective of the breeding program was to develop varieties 'ith new flower colors, consistently double flower form, and umerous flowers per plant.

The new cultivar originated from a cross made by the ıventors of the proprietary selection DIM-440 as the male r pollen parent with the proprietary selection DIM-575 as ıe female or seed parent.

The cultivar Tioga Peach was discovered and selected by ıe inventors as a flowering plant within the progeny of the :ated cross in a controlled environment in Coquille, Oreg. ,sexual reproduction of the new cultivar by terminal cut-ngs taken at Coquille, Oreg. has shown that the unique :atures of this new Impatiens are stabilized and reproduced ue to type in successive generations of asexual reproduc-on.

The following traits have been repeatedly observed and :e determined to be the unique characteristics of Tioga each. These characteristics in combination distinguish the ew Impatiens as a new and distinct cultivar:

1. Large salmon-pink flowers.
2. Flowers held above the foliage.
3. Consistently double and symmetrical flower form.
4. Numerous flowers per plant.
5. Freely branching plant habit.
6. Mounded plant form.

In comparison to the parent selection DIM-440, the new npatiens has salmon-pink compared to red flower color. In ɔmparison to the parent selection DIM-575, the new Impa-ens has salmon-pink compared to white flower color.

The new Impatiens has not been observed under all ɔssible environmental conditions. The phenotype may vary gnificantly with variations in environment such as tem-erature, light level and daylength, without, however, any ıriance in genotype.

The accompanying colored photograph illustrates the verall appearance and flower color of the new Impatiens, ıowing the colors as true as it is reasonably possible to ɔtain in colored reproductions of this type.

The photograph comprises a side perspective view of a 'pical plant of the new Impatiens grown in Salinas, Calif. etal and foliage colors in the photograph may appear fferent from the actual colors due to light reflectance.

The following observations, measurements, values, and ɔmparisons describe plants grown in Coquille, Oreg. and :eller, Tex.

2

In the following description, color references are made to The Royal Horticultural Society Colour Chart except where general terms of ordinary dictionary significance are used.

Botanical classification: *Impatiens walleriana* cultivar Tioga Peach.

Parentage:

*Male or pollen parent.*—Proprietary selection DIM-440.

*Female or seed parent.*—Proprietary selection DIM-575.

Propagation:

*Type cutting.*—Terminal cuttings.

*Time to initiate roots.*—7 to 10 days at 20C soil temperature.

*Rooting habit.*—Numerous, fibrous, and well-branched.

Plant description:

*Form.*—Mounded form, uniform, spreading and arching.

*Growth habit.*—Moderately vigorous. Freely branching, dense growth. Suitable for 10 to 25-cm containers.

*Foliage description.*—Leaves simple, generally symmetrical, abundant, and flat in aspect. Size: Length: 6.5 cm. Width: 3 cm. Shape: Ovate with acuminate tip. Texture: Smooth. Margin: Crenate. Color: Top side: 147A. Under side: 147B. Venation: Not distinctive.

*Stem color.*—Translucent, 143C with small red spots at nodes.

Flower description:

*Flower type and habit.*—Large salmon-pink flowers. Consistently double and symmetrical flowers. Freely and continuously flowering. Flower buds open similar to a rose in fullness. The flowers are borne slightly above the foliage, arising from leaf axils, at least four flowers per axil, terminal bud opening first. Numerous flowers per plant.

*Time to flower.*—Flowering generally commences four to six weeks after planting.

*Flowering season.*—Year-round under greenhouse conditions, optimal flowering during spring season in northern hemisphere.

*Flower diameter.*—3.5 cm.

*Flower depth (height).*—2 cm.

*Flower buds.*—Shape: Ovoid. Color: 38A.

*Petals.*—Quantity: At least 50 per flower. Shape: Round, oblong, or cordate with indentation at tip.

Color: Upper side, mature: Iridescent, 38A with small purple (61C) spot at base. Under side, mature: 38A. Fade: Upper and under sides fade to 38B and 38C.

*Sepals.*—Quantity: 2 per flower. Shape: Round with prominent midvein. Color: 143C.

*Spur.*—Shape: Narrow and curved. Quantity: One per flower. Length: 3 cm. Color: On bud: 144A. On open flower: 144B with red tint.

*Peduncles.*—Length: 3 cm. Color: 144A.

*Reproductive organs.*—Typical reproductive organs are not observed as these structures develop into sterile petaloids. Without the development of functional reproductive organs, pollination and subsequent seed production are not observed.

Disease resistance: No resistance or susceptibility observed.

Seed production: Seed production has not been observed.

It is claimed:

1. A new and distinct Impatiens plant named Tioga Peach, as illustrated and described.

* * * * *

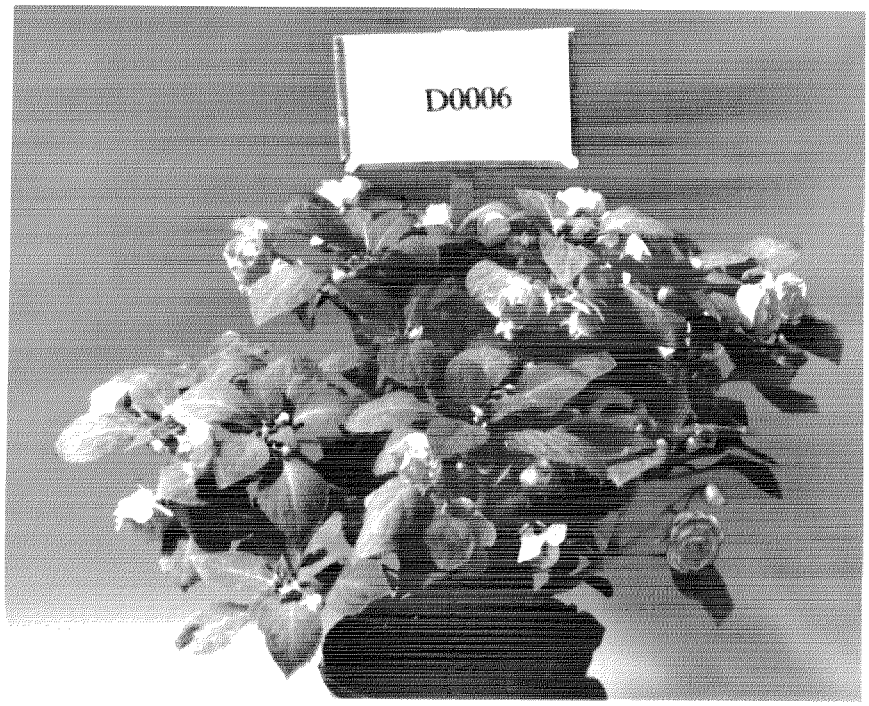
D0006